US011490799B2

(12) United States Patent
Iizuka et al.

(10) Patent No.: US 11,490,799 B2
(45) Date of Patent: Nov. 8, 2022

(54) CLEANING TOOL FOR INSERTION DEVICE (71) Applicant: OLYMPUS CORPORATION, Tokyo (JP)

(72) Inventors: Tomoyuki Iizuka, Hachioji (JP); Tomokazu Iwasaki, Hachioji (JP); Mitsuyoshi Tezuka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 147 days.

(21) Appl. No.: 16/935,551

(22) Filed: Jul. 22, 2020

(65) Prior Publication Data

US 2020/0345226 A1 Nov. 5, 2020

Related U.S. Application Data (63) Continuation of application No. PCT/JP2018/026733, filed on Jul. 17, 2018.

(30) Foreign Application Priority Data

Jan. 31, 2018 (JP) .............................. JP2018-015055

(51) Int. Cl.
*A61B 1/12* (2006.01)
*B08B 9/02* (2006.01)

(52) U.S. Cl.
CPC .............. *A61B 1/125* (2013.01); *A61B 1/122* (2013.01); *B08B 9/021* (2013.01)

(58) Field of Classification Search
CPC ......... A61B 1/121; A61B 1/122; A61B 1/123; A61B 1/125
See application file for complete search history.

(56) References Cited

U.S. PATENT DOCUMENTS

2011/0232700 A1 9/2011 Suzuki et al.
2017/0181611 A1 6/2017 Yamaya
(Continued)

FOREIGN PATENT DOCUMENTS

EP 2 347 700 A1 7/2011
EP 3 207 857 A1 8/2017
(Continued)

OTHER PUBLICATIONS

JPS565630A Machine Translation (Year: 1981).*
International Search Report dated Sep. 18, 2018 received in PCT/JP2018/026733.

*Primary Examiner* — Spencer E. Bell
(74) *Attorney, Agent, or Firm* — Scully, Scott, Murphy & Presser, P.C.

(57) ABSTRACT

A cleaning tool for insertion device includes a first fluid supply conduit, a second fluid supply conduit, a first cap component, and a second cap component, wherein a first discharge port and a third discharge port are disposed at positions where a discharging direction of fluid discharged from the first discharge port and a discharging direction of fluid discharged from the third discharge port are parallel or coaxial to each other in a vertical direction of a distal end portion of an insertion device, and a second discharge port and a fourth discharge port are disposed at positions where a discharging direction of fluid discharged from the second discharge port and a discharging direction of fluid discharged from the fourth discharge port are parallel or coaxial to each other in a lateral direction of the distal end portion of the insertion device.

18 Claims, 9 Drawing Sheets

(56) References Cited

U.S. PATENT DOCUMENTS

2017/0181612 A1   6/2017  Yamaya
2017/0182520 A1*  6/2017  Yamaya ................... B08B 3/02

FOREIGN PATENT DOCUMENTS

| | | |
|---|---|---|
| EP | 3 207 858 A1 | 8/2017 |
| JP | 56-005630 A | 1/1981 |
| JP | 03-280925 A | 12/1991 |
| JP | 6244493 B1 | 12/2017 |
| WO | 2011/030679 A1 | 3/2011 |
| WO | 2016/059920 A1 | 4/2016 |
| WO | 2016/059921 A1 | 4/2016 |
| WO | WO-2016059919 A1 *  4/2016 ............. A61B 1/122 |

* cited by examiner

CLEANING TOOL FOR INSERTION DEVICE

CROSS REFERENCE TO RELATED APPLICATION

This application is a continuation application of PCT/JP2018/026733 filed on Jul. 17, 2018 and claims benefit of Japanese Application No. 2018-015055 filed in Japan on Jan. 31, 2018, the entire contents of which are incorporated herein by this reference.

BACKGROUND OF THE INVENTION

1. Field of the Invention

The present invention relates to a cleaning tool for insertion device, and particularly to a cleaning tool for insertion device used in cleaning a distal end portion of an elongated insertion device.

2. Description of the Related Art

In a medical field, for example, elongated insertion devices, such as an endoscope, have been conventionally used for performing an operation on a desired part in a subject with the insertion device inserted in the subject.

A cleaning process using cleaning fluid, such as medicinal solution and water, is generally performed on reusable insertion devices of the above-mentioned insertion devices. For example, International Publication No. 2016/059920 discloses a cleaning tool which can be used for cleaning a distal end portion of the above-mentioned insertion device.

Specifically, International Publication No. 2016/059920 discloses a cleaning tool used for cleaning a distal end forming portion of an endoscope, the cleaning tool including a plurality of cleaning ports, a movement restricting portion, and a holding portion, fluid fed from a liquid feeding mechanism being ejected from the plurality of cleaning ports in different directions, the movement restricting portion performing positioning of the distal end forming portion to cause the fluid ejected from the plurality of cleaning ports to directly impinge on a cleaning target part in an opening portion provided in the distal end forming portion, and the holding portion being provided for holding a state where the distal end forming portion is positioned by the movement restricting portion.

SUMMARY OF THE INVENTION

One aspect of the present invention is directed to a cleaning tool for insertion device which is used in cleaning a distal end portion of an elongated insertion device with fluid for cleaning, the cleaning tool for insertion device including: a first fluid supply conduit including a first injection port, a first branching part, and a first discharge port and a second discharge port, the fluid being injected from the first injection port, the first branching part branching, into two flow passages, a flow passage through which the fluid injected from the first injection port flows, and the first discharge port and the second discharge port being provided for discharging the fluid passing through the first branching part; a second fluid supply conduit including a second injection port, a second branching part, and a third discharge port and a fourth discharge port, the fluid being injected from the second injection port, the second branching part branching, into two flow passages, a flow passage through which the fluid injected from the second injection port flows, and the third discharge port and the fourth discharge port being provided for discharging the fluid passing through the second branching part; a first cap component configured to be attachable to and detachable from the distal end portion of the insertion device, the first discharge port and the fourth discharge port being provided in the first cap component; and a second cap component configured to be attachable to and detachable from the distal end portion of the insertion device, the second discharge port and the third discharge port being provided in the second cap component, wherein the first discharge port and the third discharge port are disposed at positions where, in a state where the first cap component and the second cap component are mounted on the distal end portion of the insertion device, discharging directions of the fluid are parallel or coaxial to each other in a vertical direction of the distal end portion of the insertion device, and the second discharge port and the fourth discharge port are disposed at positions where, in a state where the first cap component and the second cap component are mounted on the distal end portion of the insertion device, discharging directions of the fluid are parallel or coaxial to each other in a lateral direction of the distal end portion of the insertion device.

DETAILED DESCRIPTION OF THE PREFERRED EMBODIMENT

Hereinafter, an embodiment of the present invention will be described with reference to drawings.

FIG. 1 to FIG. 8 are diagrams relating to the embodiment of the present invention.

Figure 1:
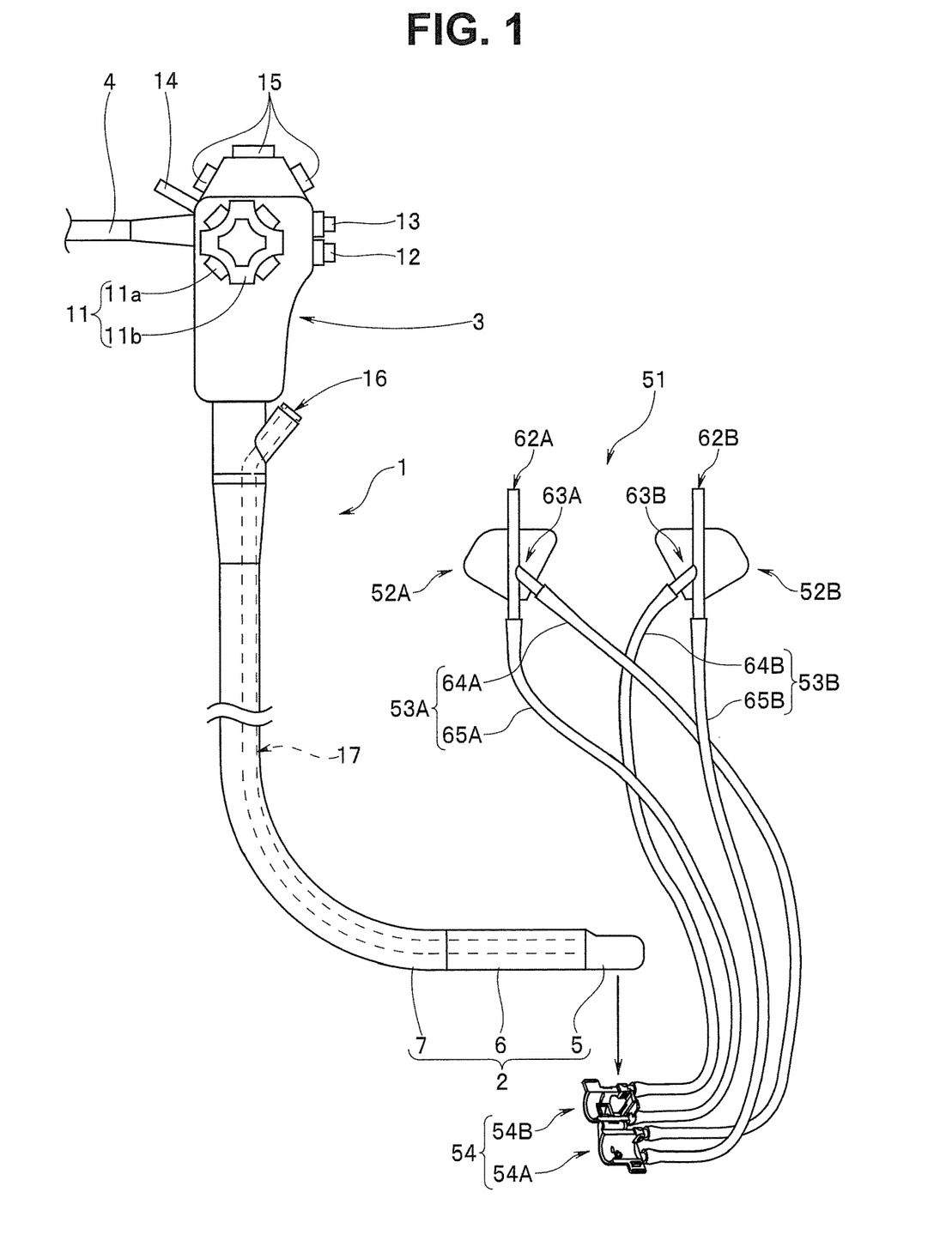
FIG. 1 is a diagram showing an external appearance configuration of an endoscope cleaning tool according to an embodiment and an endoscope which is cleaned using the endoscope cleaning tool.

An endoscope 1 is configured as an elongated insertion device which can be inserted into a subject. As shown in FIG. 1, the endoscope 1 includes an insertion portion 2, an operation portion 3, and a universal cable 4. The insertion portion 2 is formed into an elongated shape which can be inserted into a subject. The operation portion 3 is provided on a proximal end side of the insertion portion 2. The universal cable 4 extends from the operation portion 3. The endoscope 1 is configured as a side viewing endoscope, such as a duodenoscope, having a field of view in a direction intersecting with a longitudinal axis of the insertion portion 2. FIG. 1 is a diagram showing an external appearance configuration of an endoscope cleaning tool according to the embodiment and the endoscope which is cleaned using the endoscope cleaning tool.

The operation portion 3 is provided with a bending operation device 11, an air/water feeding button 12, a suction button 13, a raising base operation lever 14, and operation switches 15.

For the operation switches 15, switches, such as a freeze switch, a release switch, and an observation-mode change-over switch, are provided. The freeze switch is provided for instructing changing over of a display state of an endoscope image, obtained by picking up an image of an object by the endoscope 1, to either one of a movie or a still image. The release switch is provided for instructing recording of the endoscope image as a still image. The observation-mode change-over switch is provided for instructing changing over of an observation mode during the observation of the object with the endoscope 1.

The operation portion 3 has a treatment instrument insertion port 16 for introducing a medical device (not shown), such as an elongated treatment instrument, into a subject. One end of a treatment instrument channel tube 17 is connected to the treatment instrument insertion port 16. The other end of the treatment instrument channel tube 17 is connected to a distal end forming portion 20 (described later), which forms a distal end portion 5 of the insertion portion 2.

The insertion portion 2 is configured such that the distal end portion 5, a bending portion 6, and a flexible pipe portion 7 are provided in sequence from the distal end side of the insertion portion 2. The bending portion 6 is formed in a bendable manner. The flexible pipe portion 7 has flexibility and a large length.

The flexible pipe portion 7 includes, for example, a spiral pipe, a mesh pipe covering the spiral pipe, and a heat shrinkable tube forming an outermost layer.

The bending portion 6 includes, for example, a set of bending pieces, a metal-made mesh pipe, and bending rubber. The set of bending pieces is configured to be bendable in four directions, that is, in the upward direction, the downward direction, the leftward direction, and the rightward direction. The metal-made mesh pipe covers the set of bending pieces. The bending rubber forms an outer skin. The bending portion 6 is configured to be bendable in the upward direction or the downward direction corresponding to a rotation operation of a vertical bending knob 11a of the bending operation device 11 provided in the operation portion 3. The bending portion 6 is also configured to be bendable in the leftward direction or the rightward direction corresponding to a rotation operation of a lateral bending knob 11b of the bending operation device 11 provided in the operation portion 3.

Figure 2A:
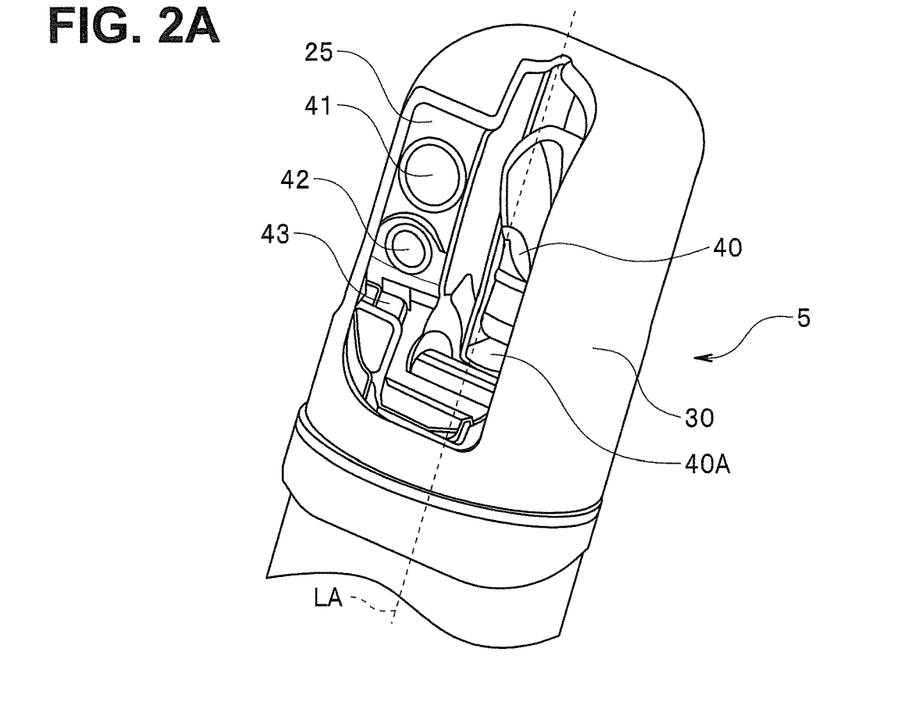
FIG. 2A is a diagram for describing one example of a configuration of a distal end portion of the endoscope.
Figure 2B:
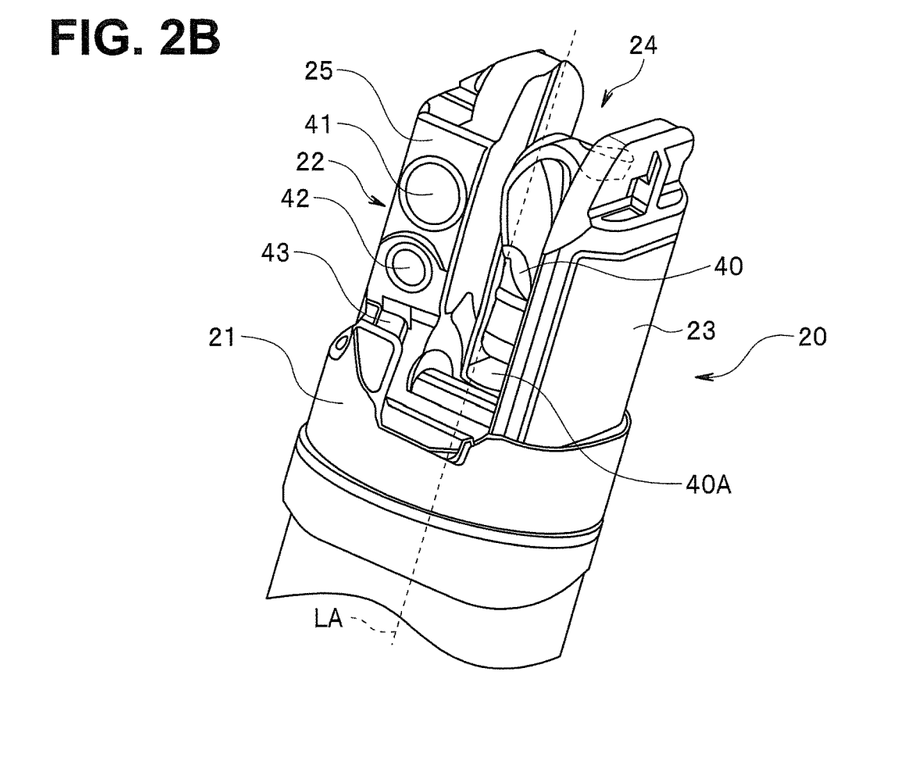
FIG. 2B is a diagram for describing one example of the configuration of the distal end portion of the endoscope.

As shown in FIG. 2A and FIG. 2B, the distal end portion 5 includes the distal end forming portion 20, and a distal end cover (hereinafter simply referred to as "cover") 30. The cover 30 is made of an insulative material, such as a resin, and is formed to be attachable to and detachable from the distal end forming portion 20. Each of FIG. 2A and FIG. 2B is a diagram for describing one example of a configuration of the distal end portion of the endoscope.

The distal end forming portion 20 includes a distal end portion body 21, an optical projecting portion 22, and a raising projecting portion 23. The distal end portion body 21 is made of an insulative material, such as a resin. The optical projecting portion 22 and the raising projecting portion 23 are made of a rigid material, such as metal.

The optical projecting portion 22 and the raising projecting portion 23 are provided to protrude from the distal end portion body 21 to a distal end side along a longitudinal axis LA of the insertion portion 2 (see FIG. 2A and FIG. 2B). Further, a raising base accommodating space 24 is provided in a gap formed between the optical projecting portion 22 and the raising projecting portion 23. The raising base accommodating space 24 is provided for turnably accommodating a raising base (forceps elevator) 40, made of a rigid material, such as metal. A treatment instrument protruding port 40A is provided in the distal end portion body 21 at a position in the vicinity of the raising base 40. The treatment instrument protruding port 40A is provided for causing a distal end portion of a medical device inserted into the treatment instrument channel tube 17 to protrude. Further, a surface of the raising base 40 has a guide surface for guiding, in a predetermined direction, a protruding direction of the distal end portion of the medical device which is caused to protrude from the treatment instrument protruding port 40A.

An upper surface 25, which is one surface of the optical projecting portion 22, is provided with an illumination lens 41 and an observation lens 42. The illumination lens 41 is provided for irradiating an object with illumination light. The observation lens 42 is provided for receiving return light emitted from the object corresponding to irradiation of the illumination light. The optical projecting portion 22 is provided with a clean nozzle 43 formed to eject fluid, supplied to the endoscope 1 corresponding to an operation of the air/water feeding button 12, toward a distal end side of the distal end forming portion 20. In other words, stain adhering to surfaces of the illumination lens 41 and the observation lens 42 is removed by the fluid ejected from the clean nozzle 43.

The raising projecting portion 23 is provided with a raising base operation wire (not shown) and a raising base motion mechanism (not shown). The raising base operation wire is towed corresponding to the operation of the raising base operation lever 14, for example. The raising base motion mechanism is formed such that the raising base 40 disposed in the raising base accommodating space 24 can be rotated and raised corresponding to a towing state of the raising base operation wire.

An endoscope cleaning tool 51 is configured as a cleaning tool for insertion device which is used in cleaning a distal end portion of an elongated insertion device with cleaning solution. Further, as shown in FIG. 1, the endoscope cleaning tool 51 includes fluid injection portions 52A, 52B, conduit portions 53A, 53B, and a cleaning cap 54 configured to be attachable to and detachable from the distal end forming portion 20 of the distal end portion 5. The cleaning cap 54 includes cap components 54A, 54B that form an inner space capable of accommodating the distal end forming portion 20 of the distal end portion 5.

The fluid injection portion 52A has an injection port 62A which is an opening from which cleaning fluid for cleaning the distal end forming portion 20 of the distal end portion 5 (hereinafter also referred to as "cleaning solution") is injected. The fluid injection portion 52A is also provided with a branching portion 63A which branches, into two flow passages, a flow passage through which the cleaning solution injected from the injection port 62A flows.

The conduit portion 53A includes two tubes 64A, 65A forming flow passages through which the cleaning solution passing through the branching portion 63A is caused to flow.

One end of the tube 64A is connected to the branching portion 63A. The other end of the tube 64A is connected to the cap component 54A. In other words, the tube 64A is formed as a conduit including a flow passage through which the cleaning solution flowing into the tube 64A through the branching portion 63A is caused to flow into the cap component 54A.

One end of the tube 65A is connected to the branching portion 63A. The other end of the tube 65A is connected to the cap component 54B. In other words, the tube 65A is formed as a conduit including a flow passage through which the cleaning solution flowing into the tube 65A through the branching portion 63A is caused to flow into the cap component 54B.

The cap component 54A is configured to discharge the cleaning solution flowing into the cap component 54A through the tube 64A and cleaning solution flowing into the cap component 54A through a tube 65B from different openings.

The fluid injection portion 52B has an injection port 62B which is an opening from which cleaning solution for cleaning the distal end forming portion 20 of the distal end portion 5 is injected. The fluid injection portion 52B is also provided with a branching portion 63B which branches, into two flow passages, a flow passage through which the cleaning solution injected from the injection port 62B flows.

The conduit portion 53B includes two tubes 64B, 65B forming flow passages through which the cleaning solution passing through the branching portion 63B is caused to flow.

One end of the tube 64B is connected to the branching portion 63B. The other end of the tube 64B is connected to the cap component 54B. In other words, the tube 64B is formed as a conduit including a flow passage through which the cleaning solution flowing into the tube 64B through the branching portion 63B is caused to flow into the cap component 54B.

One end of the tube 65B is connected to the branching portion 63B. The other end of the tube 65B is connected to the cap component 54A. In other words, the tube 65B is formed as a conduit including a flow passage through which the cleaning solution flowing into the tube 65B through the branching portion 63B is caused to flow into the cap component 54A.

The cap component 54B is configured to discharge the cleaning solution flowing into the cap component 54B through the tube 65A and the cleaning solution flowing into the cap component 54B through the tube 64B from different openings.

Figure 3:
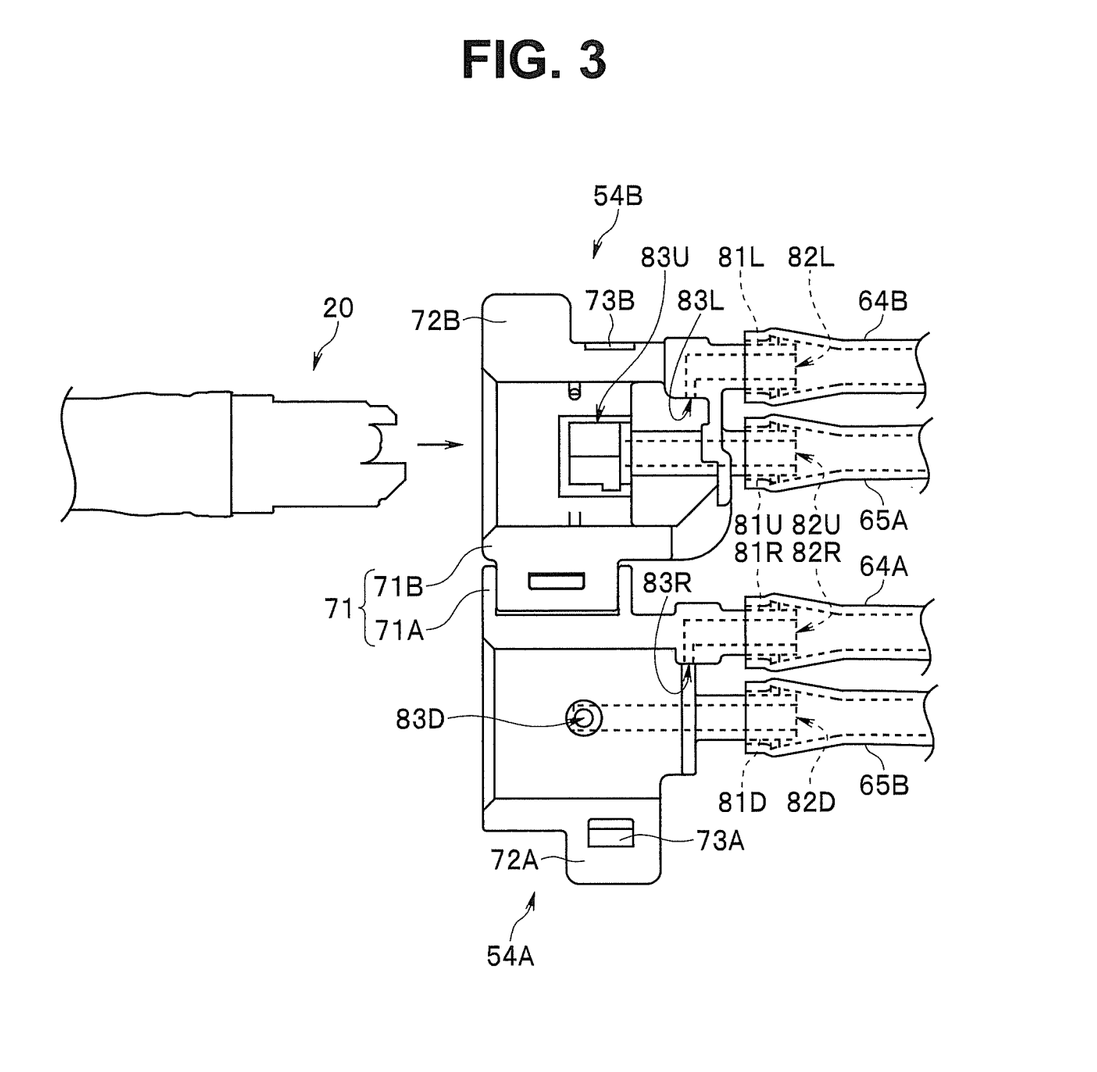
FIG. 3 is a diagram for describing a specific example of a configuration of a cap component of the endoscope cleaning tool according to the embodiment.

A specific example of a structure of the cap components 54A, 54B forming the cleaning cap 54 will be described with reference to FIG. 3 and other drawings. In FIG. 3, for the sake of convenience of illustration, a detailed structure of the distal end forming portion 20 is omitted. FIG. 3 is a diagram for describing a specific example of a configuration of the cap component of the endoscope cleaning tool according to the embodiment.

The cap component 54A is configured such that the cap component 54A is attachable to and detachable from the distal end forming portion 20, and discharge ports 83R, 83D, which will be described later, are provided in the cap component 54A. The cap component 54A is also configured such that the cap component 54A has a substantially semi-cylindrical shape, for example, and can substantially cover a lower half (a portion excluding the illumination lens 41 and the observation lens 42) of the distal end forming portion 20.

The cap component 54B is configured such that the cap component 54B is attachable to and detachable from the distal end forming portion 20, and discharge ports 83L, 83U, which will be described later, are provided in the cap component 54B. The cap component 54B is also configured such that the cap component 54B has a substantially semi-cylindrical shape, for example, and can substantially cover an upper half (a portion including the illumination lens 41 and the observation lens 42) of the distal end forming portion 20.

As shown in FIG. 3, the cap components 54A, 54B are turnably coupled by a hinge mechanism 71.

The hinge mechanism 71 includes a hinge connection portion 71A, a hinge connection portion 71B, and a hinge shaft (not shown). The hinge connection portion 71A is formed on the cap component 54A. The hinge connection portion 71B is formed on the cap component 54B. The hinge shaft corresponds to a rotation axis when the hinge connection portions 71A, 71B are rotated.

As shown in FIG. 3, a tab portion 72A is formed on the cap component 54A on a side opposite to the hinge connection portion 71A. The tab portion 72A has a shape which allows an operator, who performs a cleaning operation using the endoscope cleaning tool 51, to hold the tab portion 72A with the fingers. Further, an engaging pawl portion 73A is formed in the vicinity of the tab portion 72A.

As shown in FIG. 3, a tab portion 72B is formed on the cap component 54B on a side opposite to the hinge connection portion 71B. The tab portion 72B has a shape which allows the operator, who performs the cleaning operation using the endoscope cleaning tool 51, to hold the tab portion 72B with the fingers. Further, an engaging groove portion 73B is formed at a position adjacent to the tab portion 72B, and the engaging groove portion 73B has a shape which allows the engaging groove portion 73B to engage with the engaging pawl portion 73A.

The cap components 54A, 54B are configured to form the cleaning cap 54 which, in a state where the engaging pawl portion 73A and the engaging groove portion 73B engage with each other, has an inner space capable of accommodating the distal end forming portion 20, and allows the distal end forming portion 20 to be fixed and disposed at a predetermined position in the inner space. In other words, the cap components 54A, 54B are configured to form the inner space capable of accommodating the distal end forming portion 20 in a state where the engaging pawl portion 73A and the engaging groove portion 73B engage with each other.

The cap component 54A has a tube connecting conduit 81R and a tube connecting conduit 81D. The tube connecting conduit 81R is formed such that the tube connecting conduit 81R can be inserted into and connected to the other end of the tube 64A. The tube connecting conduit 81D is formed such that the tube connecting conduit 81D can be inserted into and connected to the other end of the tube 65B.

The tube connecting conduit 81R has an inflow port 82R and the discharge port 83R. The inflow port 82R is an opening from which the cleaning solution arriving at the other end of the tube 64A flows into the tube connecting conduit 81R. The discharge port 83R is an opening for discharging the cleaning solution, flowing into the tube connecting conduit 81R from the inflow port 82R, at a predetermined position adjacent to the other end of the tube 64A. The tube connecting conduit 81R also has a flow passage for setting a discharging direction of the cleaning solution, discharged from the discharge port 83R, in a direction orthogonal to a flow direction of the cleaning solution flowing into the tube connecting conduit 81R from the inflow port 82R. With such a configuration, the cleaning solution flowing into the tube connecting conduit 81R through the inflow port 82R can be discharged toward the tab portion 72A from the discharge port 83R provided at a position close to the hinge connection portion 71A.

The tube connecting conduit 81D has an inflow port 82D and the discharge port 83D. The inflow port 82D is an opening from which the cleaning solution arriving at the other end of the tube 65B flows into the tube connecting conduit 81D. The discharge port 83D is an opening for discharging the cleaning solution, flowing into the tube connecting conduit 81D from the inflow port 82D, at a predetermined position on an inner wall of the cap component 54A, the predetermined position being away from the other end of the tube 64A. The tube connecting conduit 81D also has a flow passage for setting a discharging direction of the cleaning solution, discharged from discharge port 83D, in a direction orthogonal to a flow direction of the cleaning solution flowing into the tube connecting conduit 81D from the inflow port 82D, and which is skewed with respect to the discharging direction of the cleaning solution discharged from the discharge port 83R.

The cap component 54B has a tube connecting conduit 81L and a tube connecting conduit 81U. The tube connecting conduit 81L is formed such that the tube connecting conduit 81L can be inserted into and connected to the other end of the tube 64B. The tube connecting conduit 81U is formed such that the tube connecting conduit 81U can be inserted into and connected to the other end of the tube 65A.

The tube connecting conduit 81L has an inflow port 82L and the discharge port 83L. The inflow port 82L is an opening from which the cleaning solution arriving at the other end of the tube 64B flows into the tube connecting conduit 81L. The discharge port 83L is an opening for discharging the cleaning solution, flowing into the tube connecting conduit 81L from the inflow port 82L, at a predetermined position adjacent to the other end of the tube 64B. The tube connecting conduit 81L also has a flow passage for setting a discharging direction of the cleaning solution, discharged from the discharge port 83L, in a direction orthogonal to a flow direction of the cleaning solution flowing into the tube connecting conduit 81L from the inflow port 82L. With such a configuration, the cleaning solution flowing into the tube connecting conduit 81L through the inflow port 82L can be discharged toward the hinge connection portion 71B from the discharge port 83L provided at a position close to the tab portion 72B.

The tube connecting conduit 81U has an inflow port 82U and the discharge port 83U. The inflow port 82U is an opening from which the cleaning solution arriving at the other end of the tube 65A flows into the tube connecting conduit 81U. The discharge port 83U is an opening for discharging the cleaning solution, flowing into the tube connecting conduit 81U from the inflow port 82U, at a predetermined position on an inner wall of the cap component 54B, the predetermined position being away from the other end of the tube 64A. The tube connecting conduit 81U also has a flow passage for setting a discharging direction of the cleaning solution, discharged from the discharge port 83U, in a direction orthogonal to a flow direction of the cleaning solution flowing into the tube connecting conduit 81U from the inflow port 82U, and which is skewed with respect to the discharging direction of the cleaning solution discharged from the discharge port 83L.

As described above, the endoscope cleaning tool 51 includes a fluid supply conduit PA (not shown) having the injection port 62A, the branching portion 63A, and the discharge ports 83R, 83U. The branching portion 63A branches the flow passage, through which fluid (cleaning solution) injected from the injection port 62A flows, into two flow passages respectively communicating with the tubes 64A, 65A. The discharge ports 83R, 83U are provided for discharging, in the cleaning cap 54, the fluid flowing through the two flow passages after passing through the branching portion 63A. As described above, the endoscope cleaning tool 51 also includes a fluid supply conduit PB (not shown) having the injection port 62B, the branching portion 63B, and the discharge ports 83L, 83D. The branching portion 63B branches the flow passage, through which fluid (cleaning solution) injected from the injection port 62B flows, into two flow passages respectively communicating with the tubes 64B, 65B. The discharge ports 83L, 83D are provided for discharging, in the cleaning cap 54, the fluid flowing through the two flow passages after passing through the branching portion 63B. In other words, the fluid supply conduit PA of the endoscope cleaning tool 51 is formed of the fluid injection portion 52A, the tubes 64A, 65A of the conduit portion 53A, the tube connecting conduit 81R of the cap component 54A, and the tube connecting conduit 81U of the cap component 54B. The fluid supply conduit PB of the endoscope cleaning tool 51 is formed of the fluid injection portion 52B, the tubes 64B, 65B of the conduit portion 53B, the tube connecting conduit 81D of the cap component 54A, and the tube connecting conduit 81L of the cap component 54B.

In the endoscope cleaning tool 51 of the present embodiment, the discharge port 83R of the fluid supply conduit PA is provided in the cap component 54A, and the discharge port 83U of the fluid supply conduit PA is provided in the cap component 54B. Further, in the endoscope cleaning tool 51 of the present embodiment, the discharge port 83L of the fluid supply conduit PB is provided in the cap component 54B, and the discharge port 83U of the fluid supply conduit PB is provided in the cap component 54A. In other words, in the endoscope cleaning tool 51 of the present embodiment, two discharge ports of one fluid supply conduit are respectively provided in the cap components 54A, 54B.

In the endoscope cleaning tool 51 of the present embodiment, each of the fluid injection portion 52A, which forms the fluid supply conduit PA, and the fluid injection portion 52B, which forms the fluid supply conduit PB, is formed from a common component having the same shape. Further, in the endoscope cleaning tool 51 of the present embodiment, each of the conduit portion 53A, which forms the fluid supply conduit PA, and the conduit portion 53B, which forms the fluid supply conduit PB, is formed from a common component having the same shape. In other words, in the endoscope cleaning tool 51 of the present embodiment, at least a portion of each of the fluid supply conduits PA, PB is formed from the common component.

Next, the description will be made for a specific example of the cleaning operation performed when the distal end portion 5 (the distal end forming portion 20) is cleaned using the endoscope cleaning tool 51.

An operator removes the cover 30 mounted on the distal end portion 5 of the used endoscope 1 to cause the distal end forming portion 20 to be exposed. Thereafter, the operator rotates the insertion portion 2 about the longitudinal axis LA, for example, so that the distal end forming portion 20 in a state of facing in a predetermined direction is disposed in one cap component of the cap components 54A, 54B (for example, the cap component 54A).

Figure 4:
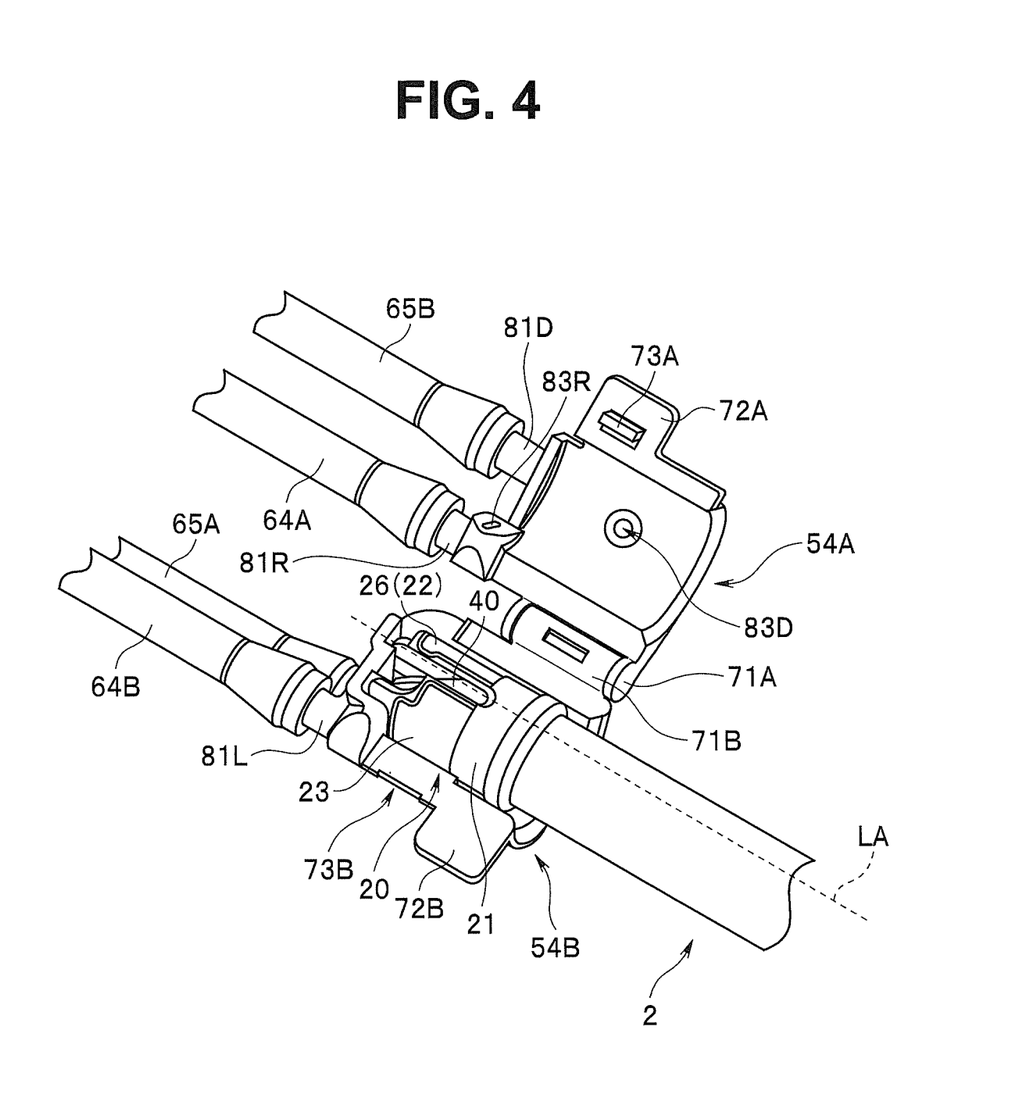
FIG. 4 is a diagram showing a state in the course of mounting a cleaning cap of the endoscope cleaning tool according to the embodiment on a distal end forming portion of the endoscope.

Specifically, the operator disposes the distal end forming portion 20 in the cap component 54B with the upper surface 25 of the optical projecting portion 22 facing toward the discharge port 83U and a side surface of the raising projecting portion 23 facing toward the discharge port 83L, for example. With such an operation performed by the operator, the distal end forming portion 20 is disposed in the cap component 54B in a state shown in FIG. 4, for example. FIG. 4 is a diagram showing a state in the course of mounting the cleaning cap of the endoscope cleaning tool according to the embodiment on the distal end forming portion of the endoscope.

The operator disposes the distal end forming portion 20 in a state of facing in a predetermined direction in the one cap component (for example, the cap component 54A). Thereafter, as an operation for causing the engaging pawl portion 73A and the engaging groove portion 73B to engage with each other, the operator performs an operation of causing the hinge connection portion to be rotated while the operator holds the tab portion provided on the other cap component of the cap components 54A, 54B (for example, the cap component 54B) with the fingers, for example.

Specifically, the operator disposes the distal end forming portion 20 in a state of facing in the above-mentioned direction, for example, in the cap component 54B. Thereafter, the operator performs an operation of causing the hinge connection portion 71A to be rotated while the operator holds the tab portion 72A provided on the cap component 54A with the fingers, so that the engaging pawl portion 73A and the engaging groove portion 73B engage with each other. With such operations performed by the operator, a lower surface 26 (see FIG. 4), which is a surface of the optical projecting portion 22 on a side opposite to the upper surface 25, is caused to face toward the discharge port 83D, and a side surface of the optical projecting portion 22 is caused to face toward the discharge port 83R.

Figure 5A:
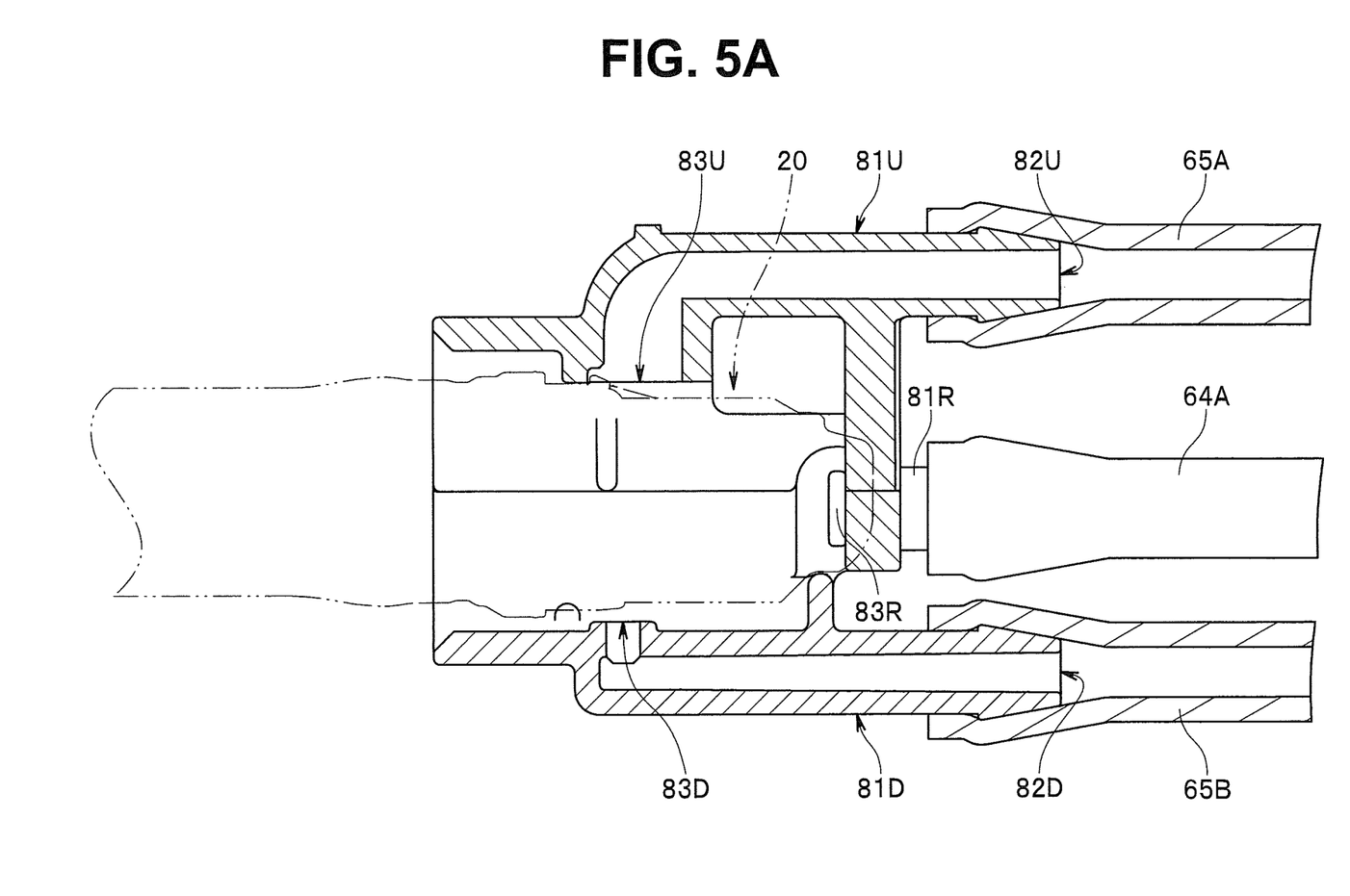
FIG. 5A is a cross-sectional view of the cleaning cap of the endoscope cleaning tool according to the embodiment as viewed in a side view.
Figure 5B:
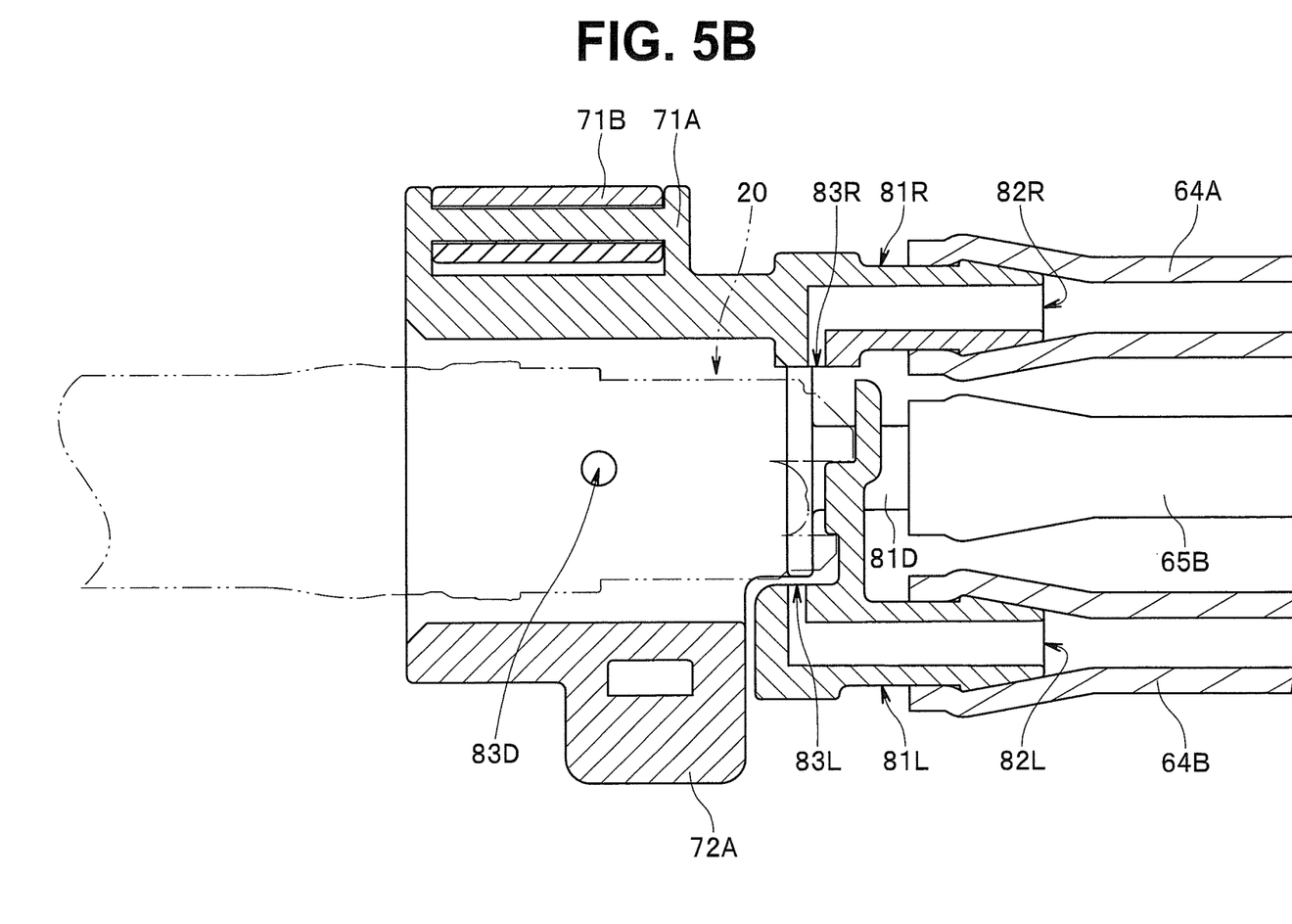
FIG. 5B is a cross-sectional view of the cleaning cap of the endoscope cleaning tool according to the embodiment as viewed in a top view.

In other words, with the above-mentioned operations performed by the operator, the distal end forming portion 20 is disposed in a state shown in FIG. 5A and FIG. 5B in the inner space of the cleaning cap 54, formed of the cap components 54A, 54B. In FIGS. 5A and 5B, for the sake of convenience of illustration, a detailed structure of the distal end forming portion 20 is omitted. FIG. 5A is a cross-sectional view of the cleaning cap of the endoscope cleaning tool according to the embodiment as viewed in a side view. FIG. 5B is a cross-sectional view of the cleaning cap of the endoscope cleaning tool according to the embodiment as viewed in a top view.

Figure 6:
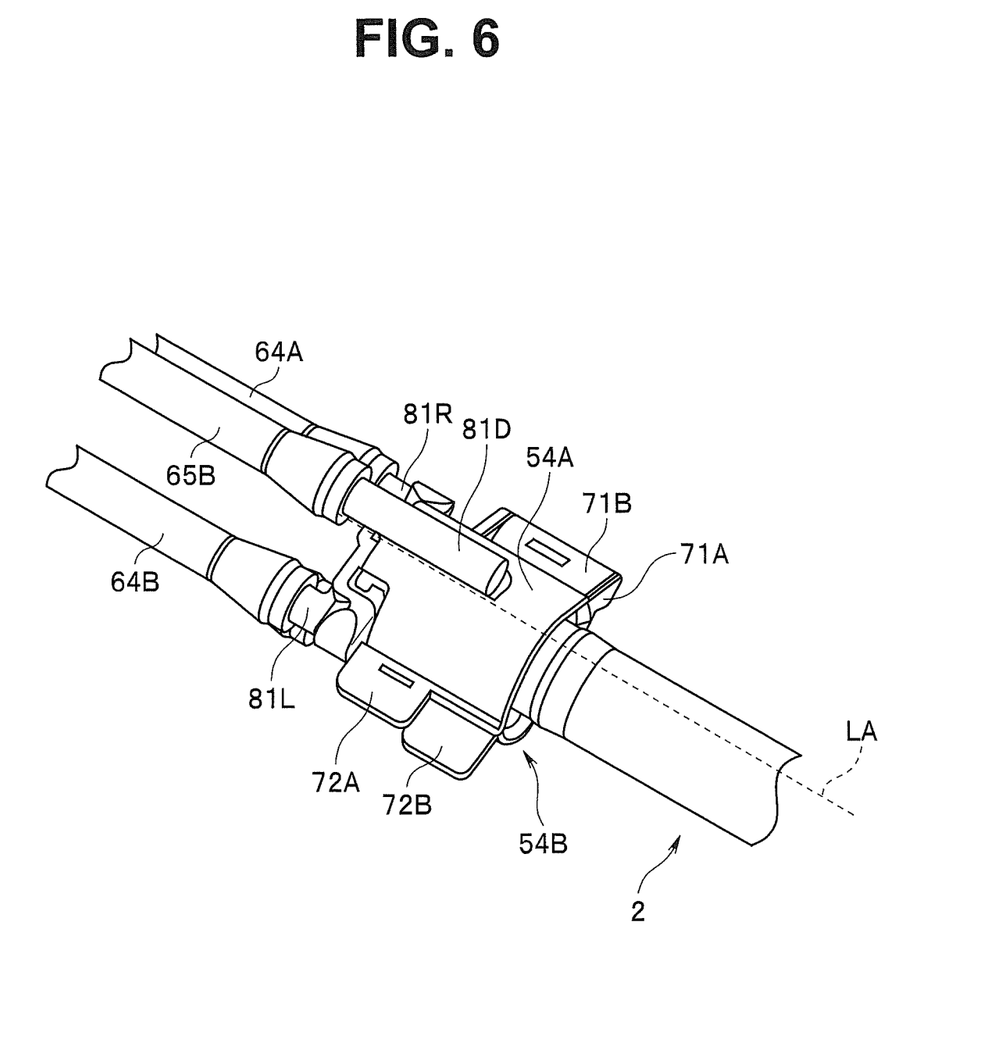
FIG. 6 is a diagram showing a state where the cleaning cap of the endoscope cleaning tool according to the embodiment is mounted on the distal end portion of the endoscope.

The operator performs the above-mentioned operations to mount the cleaning cap 54 on the distal end forming portion 20 in a state shown in FIG. 6 and, thereafter, performs an operation for injecting cleaning solution from the injection ports 62A, 62B using an instrument, such as a syringe. FIG. 6 is a diagram showing a state where the cleaning cap of the endoscope cleaning tool according to the embodiment is mounted on the distal end portion of the endoscope.

In other words, the discharge ports 83R, 83U are disposed in a positional relationship where, when the cleaning cap 54 (the cap components 54A, 54B) is mounted on the distal end forming portion 20, the discharge ports 83R, 83U are disposed around the longitudinal axis LA of the insertion portion 2, and the respective directions of fluid (cleaning solution) are skewed with respect to each other. The discharge ports 83L, 83D are disposed in a positional relationship where, when the cleaning cap 54 (the cap components 54A, 54B) is mounted on the distal end forming portion 20, the discharge ports 83L, 83D are disposed around the longitudinal axis LA of the insertion portion 2, and the respective discharging directions of fluid (cleaning solution) are skewed with respect to each other. Further, the discharge ports 83R, 83L are disposed in a positional relationship where, when the cleaning cap 54 (the cap components 54A, 54B) is mounted on the distal end forming portion 20, the respective discharging directions of fluid (cleaning solution) are parallel or coaxial to each other. The discharge ports 83U, 83D are disposed in a positional relationship where, when the cleaning cap 54 (the cap components 54A, 54B) is mounted on the distal end forming portion 20, the respective discharging directions of fluid (cleaning solution) are parallel or coaxial to each other.

Figure 7:
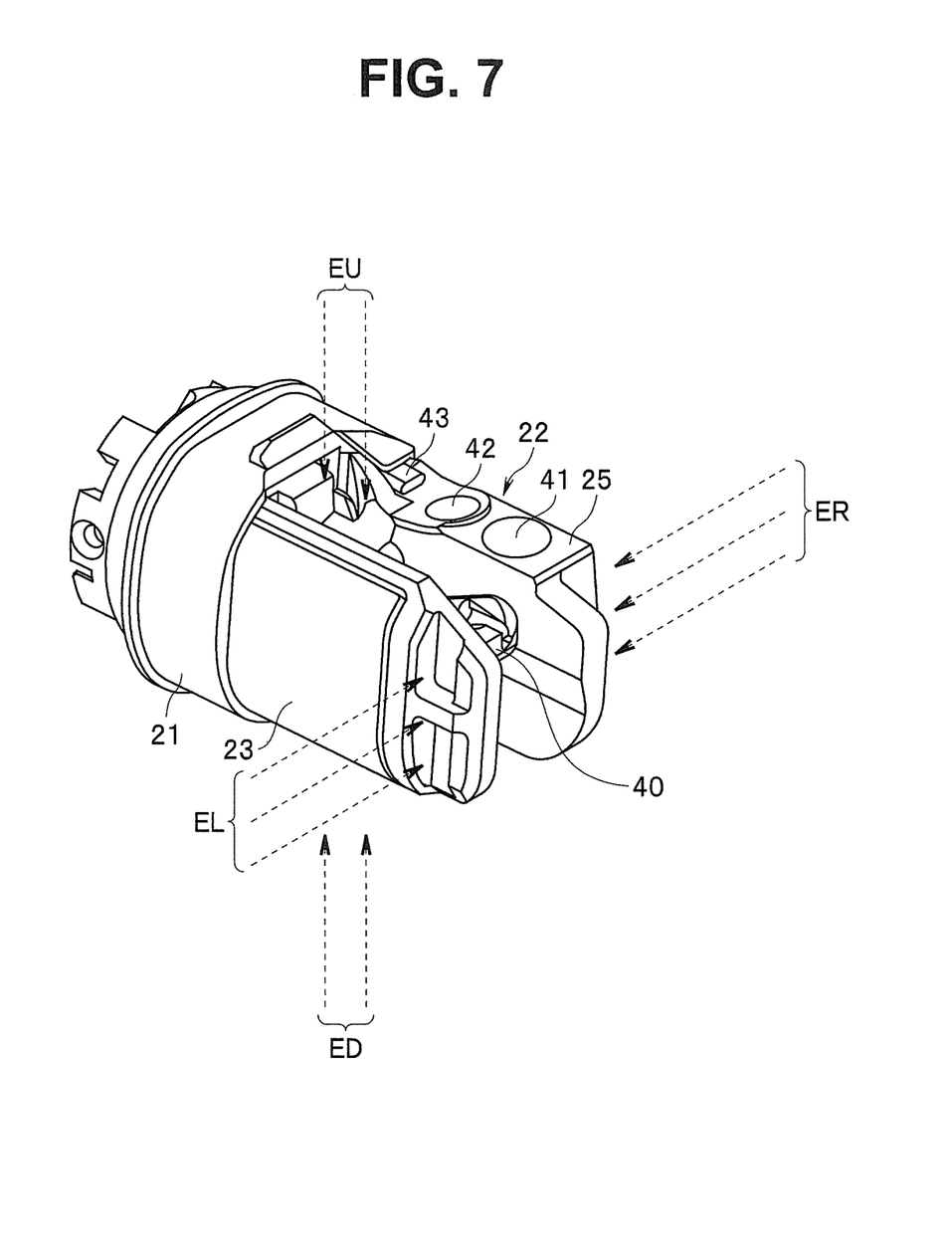
FIG. 7 is a diagram for describing discharging directions of fluids discharged through discharge ports provided in the cleaning cap of the endoscope cleaning tool according to the embodiment.

The cleaning solution injected from the injection port 62A passes through the branching portion 63A and, thereafter, flows through two flow passages consisting of the tubes 64A, 65A, and is discharged from two openings consisting of the discharge ports 83R, 83U simultaneously. Then, the cleaning solution passing through the discharge port 83R is discharged in a discharging direction indicated by arrows ER in FIG. 7, and removes stain adhering to a right surface side of the distal end forming portion 20 including the side surface of the optical projecting portion 22. The cleaning solution passing through the discharge port 83U is discharged in a discharging direction indicated by arrows EU in FIG. 7, and removes stain adhering to an upper surface side of the distal end forming portion 20 including the guide surface of the raising base 40. FIG. 7 is a diagram for describing the discharging directions of fluids discharged through the discharge ports provided in the cleaning cap of the endoscope cleaning tool according to the embodiment.

The cleaning solution injected from the injection port 62B passes through the branching portion 63B and, thereafter, flows through two flow passages consisting of the tubes 64B, 65B, and is discharged from two openings consisting of the discharge ports 83L, 83D simultaneously. Then, the cleaning solution passing through the discharge port 83L is discharged in a discharging direction indicated by arrows EL in FIG. 7, and removes stain adhering to a left surface side of the distal end forming portion 20 including the side surface of the raising projecting portion 23. The cleaning solution passing through the discharge port 83D is discharged in a discharging direction indicated by arrows ED in FIG. 7, and removes stain adhering to a lower surface side of the distal end forming portion 20 including a back side of the guide surface of the raising base 40.

As described above, according to the present embodiment, in the inner space of the cleaning cap 54 formed of the cap components 54A, 54B, the cleaning solution passing through the discharge port 83R and the cleaning solution passing through the discharge port 83U are discharged in the respective discharging directions having a positional relationship where the discharging direction of the cleaning solution passing through the discharge port 83R and the discharging direction of the cleaning solution passing through the discharge port 83U are skewed with respect to each other. As also described above, according to the present embodiment, when the cleaning solution is injected from the injection port 62A, it is possible to simultaneously clean the upper surface side and the right surface side of the distal end forming portion 20 disposed in the inner space of the cleaning cap 54. Therefore, according to the present embodiment, it is possible to cause the cleaning solution passing through the discharge port 83R and the cleaning solution passing through the discharge port 83U to respectively impinge on predetermined two positions of the distal end forming portion 20 simultaneously without causing interference and hence, as a result, the distal end forming portion 20 can be efficiently cleaned.

Further, according to the present embodiment, for example, when the operator injects water from the injection port 62A before the operator mounts the cleaning cap 54 on the distal end forming portion 20, it is possible to individually check a clogging state in two flow passages, consisting of the flow passage ranging from the tube 64A to the discharge port 83R of the cap component 54A and the flow passage ranging from the tube 65A to the discharge port 83U of the cap component 54B. Therefore, according to the present embodiment, clogging in the two flow passages through which the cleaning solution injected from the injection port 62A flows can be removed with certainty and hence, as a result, the distal end forming portion 20 can be efficiently cleaned.

As described above, according to the present embodiment, in the inner space of the cleaning cap 54 formed of the cap components 54A, 54B, the cleaning solution passing through the discharge port 83L and the cleaning solution passing through the discharge port 83D are discharged in the respective discharging directions having a positional relationship where the discharging direction of the cleaning solution passing through the discharge port 83L and the discharging direction of the cleaning solution passing through the discharge port 83D are skewed with respect to each other. As also described above, according to the present embodiment, when the cleaning solution is injected from the injection port 62B, it is possible to simultaneously clean the lower surface side and the left surface side of the distal end forming portion 20 disposed in the inner space of the cleaning cap 54. Therefore, according to the present embodiment, it is possible to cause the cleaning solution passing through the discharge port 83L and the cleaning solution passing through the discharge port 83D to respectively impinge on predetermined two positions of the distal end forming portion 20 simultaneously without causing interference and hence, as a result, the distal end forming portion 20 can be efficiently cleaned.

Further, according to the present embodiment, for example, when the operator injects water from the injection port 62B before the operator mounts the cleaning cap 54 on the distal end forming portion 20, it is possible to individually check a clogging state in two flow passages, consisting of the flow passage ranging from the tube 64B to the discharge port 83L of the cap component 54B and the flow passage ranging from the tube 65B to the discharge port 83D of the cap component 54A. Therefore, according to the present embodiment, clogging in the two flow passages through which the cleaning solution injected from the injection port 62B flows can be removed with certainty and hence, as a result, the distal end forming portion 20 can be efficiently cleaned.

Figure 8:
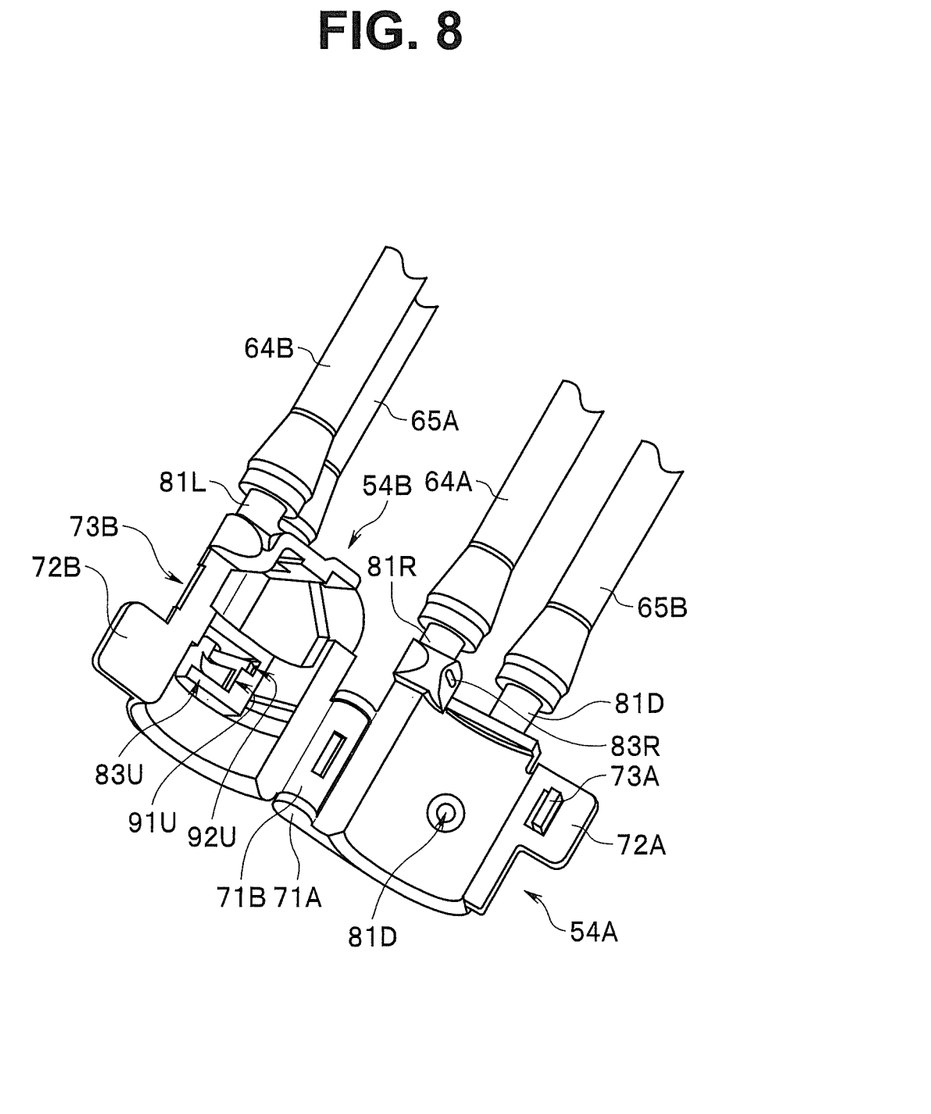
FIG. 8 is a diagram for describing the configuration of the cap component of the endoscope cleaning tool according to the embodiment.

In the present embodiment, for example, as shown in FIG. 8, steps are provided on a portion of an inner wall of the discharge port 83U for branching the discharging direction of the cleaning solution passing through the tube connecting conduit 81U into two directions which are parallel to each other, that is, in a direction along an inner wall portion 91U and a direction along an inner wall portion 92U. With such a configuration, it is possible to expand a region (of the upper surface side of the distal end forming portion 20) which is mainly cleaned with the cleaning solution discharged from the discharge port 83U, for example. Further, with the above-mentioned configuration, it is possible to easily visually recognize whether or not the discharging direction of the cleaning solution passing through the tube connecting conduit 81U, for example, is branched into two directions and hence, a burden on an operation of inspecting the discharge port 83U can be reduced. FIG. 8 is a diagram for describing the configuration of the cap component of the endoscope cleaning tool according to the embodiment.

In the present embodiment, for example, the fluid supply conduit PA may be formed such that the flow passage ranging from the branching portion 63A to the discharge port 83R and the flow passage ranging from the branching portion 63A to the discharge port 83U have substantially the same capacity. With such a configuration, when the cleaning solution is injected from the injection port 62A, an amount of the cleaning solution impinging on the upper surface side of the distal end forming portion 20 and an amount of the cleaning solution impinging on the right surface side of the distal end forming portion 20 can be set substantially equal to each other and hence, as a result, it is possible to further efficiently clean the distal end forming portion 20.

In the present embodiment, for example, the fluid supply conduit PB may be formed such that the flow passage ranging from the branching portion 63B to the discharge port 83L and the flow passage ranging from the branching portion 63B to the discharge port 83D have substantially the same capacity. With such a configuration, when the cleaning solution is injected from the injection port 62B, an amount of the cleaning solution impinging on the lower surface side of the distal end forming portion 20 and an amount of the cleaning solution impinging on the left surface side of the distal end forming portion 20 can be set substantially equal to each other and hence, as a result, it is possible to further efficiently clean the distal end forming portion 20.

Further, in the present embodiment, for example, each of the injection ports 62A, 62B may be formed into a shape which allows connection of a syringe of a luer-lock type. With such a configuration, for example, cleaning solution can be injected in a state where a syringe connected to the injection port 62A and a syringe connected to the injection port 62B are fixed and hence, as a result, it is possible to improve operational efficiency in performing an operation of injecting the cleaning solution.

The configuration in the present embodiment is not limited to that the fluid injection portions 52A, 52B are separated components. The fluid injection portions 52A, 52B may be configured as an integral component. With such a configuration, cleaning solution can be injected in a state where the injection ports 62A, 62B are close to each other, for example, and hence, as a result, it is possible to improve operational efficiency in performing an operation of injecting the cleaning solution.

The endoscope cleaning tool 51 of the present embodiment is not limited to the configuration where the cleaning solution injected from one injection port is discharged from two discharge ports. For example, the endoscope cleaning tool 51 of the present embodiment may be configured such that the cleaning solution injected from the one injection port is discharged from three or more discharge ports. In other words, it is sufficient for the fluid supply conduit of the endoscope cleaning tool 51 of the present embodiment to include the injection port, the branching portion, and the plurality of discharge ports, cleaning fluid (cleaning solution) for cleaning the distal end forming portion 20 being injected from the injection port, the branching portion branching the flow passage, through which the fluid injected from the injection port flows, into the plurality of flow passages, and the plurality of discharge ports being provided for discharging, in the cleaning cap 54, the fluid flowing through the plurality of flow passages after passing through the branching portion. Further, the endoscope cleaning tool 51 of the present embodiment may include one fluid supply conduit, or may include a plurality of fluid supply conduits.

The configuration of the endoscope cleaning tool 51 of the present embodiment may be suitably modified to allow cleaning of a distal end portion of a medical device, such as a treatment instrument configured as an elongated insertion device which can be inserted into a subject, for example.

The configuration of the endoscope cleaning tool 51 of the present embodiment may be suitably modified to have a positional relationship where, when the cap components 54A, 54B are mounted on the distal end forming portion 20, the discharging directions of fluid (cleaning solution) discharged from two discharge ports of the fluid supply conduit intersect with each other. Specifically, the discharge ports 83R, 83U (of the fluid supply conduit PA) may be disposed in a positional relationship where, when the cap components 54A, 54B are mounted on the distal end forming portion 20, the discharging direction of fluid (cleaning solution) discharged from the discharge port 83R and the discharging direction of fluid (cleaning solution) discharged from the discharge port 83U intersect with each other. Further, the discharge ports 83L, 83D (of the fluid supply conduit PB) may be disposed in a positional relationship where, when the cap components 54A, 54B are mounted on the distal end forming portion 20, the discharging direction of fluid (cleaning solution) discharged from the discharge port 83L and the discharging direction of fluid (cleaning solution) discharged from the discharge port 83D intersect with each other.

The present invention is not limited to the above-mentioned embodiment, and it goes without saying that various modifications and applications are conceivable without departing from the gist of the invention.

What is claimed is:

1. A cleaning tool comprising:
    a first fluid supply conduit comprising:
       a first injection port,
       a first branching part,
       a first flow passage in fluid communication with a first portion of the first branching part and a second flow passage in fluid communication with a second portion of the first branching part, and
       a first discharge port terminating at the first flow passage and a second discharge port terminating at the second flow passage,
    the first fluid supply conduit being configured such that fluid injected into the first injection port is separated by the first branching part to flow into the first and second flow passages and ejected from the first and second discharge ports;
    a second fluid supply conduit comprising:
       a second injection port,
       a second branching part,
       a third flow passage in fluid communication with a first portion of the second branching part and a fourth flow passage in fluid communication with a second portion of the second branching part, and
       a third discharge port terminating at the third flow passage and a fourth discharge port terminating at the fourth flow passage,
    the second fluid supply conduit being configured such that fluid injected into the second injection port is separated by the second branching part to flow into the third and fourth flow passages and ejected from the third and fourth discharge ports; and
    a cap configured to be attachable to and detachable from a distal end portion of an insertion device, the cap comprising:
       a first cap component having the first discharge port and the fourth discharge port; and
       a second cap component movable relative to the first cap component, the second cap component having the second discharge port and the third discharge port,
    wherein the cap is configured to move between a first open state and a second closed state to attach to the distal end portion of the insertion device; and
    in the second closed state:
       fluid ejected from the first discharge port is directed in a first direction and fluid ejected from the third discharge port is directed in a third direction opposing the first direction, and
       fluid ejected from the second discharge port is directed in a second direction and fluid ejected from and the fourth discharge port is directed in a fourth direction opposing the second direction.

2. The cleaning tool according to claim 1, wherein, in the second closed state, the first and second directions are skewed with respect to each other or intersect with each other.

3. The cleaning tool according to claim 2, wherein, in the second closed state, the third and fourth directions are skewed with respect to each other or intersect with each other.

4. The cleaning tool according to claim 1, wherein the first cap component and the second cap component are configured to define an inner space configured to accommodate the distal end portion of the insertion device.

5. The cleaning tool according to claim 1, wherein, in the second closed state, the first discharge port and the third discharge port are disposed at positions closer to a distal end of the insertion device in a longitudinal direction of the insertion device than the second discharge port and the fourth discharge port.

6. The cleaning tool according to claim 1, wherein, in the first fluid supply conduit, the first flow passage and the second flow passage have substantially a same fluid capacity.

7. The cleaning tool according to claim 6, wherein, in the second fluid supply conduit, the third flow passage and the fourth flow passage have substantially a same fluid capacity.

8. The cleaning tool according to claim 1, wherein the first cap component and the second cap component are attachable to and detachable from each other.

9. The cleaning tool according to claim 1, wherein the first direction, the second direction, the third direction and the fourth direction each intersect with a longitudinal axis of the insertion device when the cap is in the second state.

10. The cleaning tool according to claim 1, where an inner surface of the second cap component having steps surrounding the second discharge port to branch fluid from the second discharge port to eject towards two directions.

11. A cleaning tool comprising:
    a first fluid supply conduit in fluid communication with a first discharge port;
    a second fluid supply conduit in fluid communication with a second discharge port; and
    a cap configured to be attachable to and detachable from a distal end portion of an insertion device, the cap comprising a first cap component having the first discharge port and a second cap component having the second discharge port;

wherein the first cap component being movable relative to the second cap component to attach the cap to the distal end portion of the insertion device;

fluid ejected from the first and second discharge ports impinge on the distal end portion from different directions when the cap is attached to the distal end portion of the insertion device; and an inner surface of the second cap component having a step surrounding the second discharge port to branch fluid from the second discharge port to eject towards two directions.

12. The cleaning tool according to claim 11, wherein, when the cap is attached to the distal end portion of the insertion device, the fluid ejected from different directions are skewed with respect to each other or intersect with each other.

13. The cleaning tool according to claim 12, wherein, when the cap is attached to the distal end portion of the insertion device, the first discharge port is disposed at a position closer to a distal end of the insertion device in a longitudinal direction of the insertion device than the second discharge port.

14. The cleaning tool according to claim 11, wherein the first cap component and the second cap component are attachable to and detachable from each other.

15. A cleaning tool comprising:

a cap including a first cap and a second cap, the first cap being configured to attach to and detach from the second cap, wherein the cap is configured to define a space between the first cap and the second cap when the first cap is attached to the second cap;

the first cap having a first discharge port;

the second cap having a second discharge port;

wherein the first discharge port and the second discharge port oppose each other across the space; and an inner surface of the second cap having a step surrounding the second discharge port to branch fluid from the second discharge port to eject towards two directions.

16. The cleaning tool according to claim 15, wherein:

the first cap has the first discharge port and a third discharge port;

the second cap has the second discharge port and a fourth discharge port;

wherein the first discharge port and the fourth discharge port face each other across the space; and the second discharge port and the third discharge port face each other across the space.

17. The cleaning tool according to claim 15, wherein the first discharge port is disposed at a position closer to a distal end of the cap in a longitudinal direction of the cap than the second discharge port.

18. The cleaning tool according to claim 15, wherein the first cap and the second cap are attachable to and detachable from each other.

* * * * *